(12) United States Patent
Yamaguchi et al.

(10) Patent No.: US 8,637,716 B2
(45) Date of Patent: Jan. 28, 2014

(54) PROCESSES FOR PRODUCTION OF ISOBUTENE AND TERTIARY BUTANOL

(75) Inventors: Tatsuo Yamaguchi, Chiyoda-ku (JP); Hiroyuki Noda, Chiyoda-ku (JP); Toru Watanabe, Chiyoda-ku (JP); Shumya Kirino, Chiyoda-ku (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 1196 days.

(21) Appl. No.: 12/091,016

(22) PCT Filed: Oct. 25, 2006

(86) PCT No.: PCT/JP2006/321215
§ 371 (c)(1),
(2), (4) Date: Apr. 21, 2008

(87) PCT Pub. No.: WO2007/052505
PCT Pub. Date: May 10, 2007

(65) Prior Publication Data
US 2009/0124835 A1    May 14, 2009

(30) Foreign Application Priority Data

Nov. 1, 2005   (JP) ................. 2005-317904
Dec. 27, 2005  (JP) ................. 2005-373789

(51) Int. Cl.
*C07C 29/04*   (2006.01)

(52) U.S. Cl.
USPC ..................... 568/895; 568/898; 568/899

(58) Field of Classification Search
USPC ................ 502/24; 568/898, 700, 899, 895
See application file for complete search history.

(56) References Cited

U.S. PATENT DOCUMENTS

| | | | |
|---|---|---|---|
| 3,665,048 A | | 5/1972 | Grane et al. |
| 4,236,034 A | * | 11/1980 | Aoshima et al. ............ 568/898 |
| 4,351,971 A | | 9/1982 | Kanemaru et al. |
| 4,395,580 A | | 7/1983 | Juguin et al. |
| 4,423,271 A | | 12/1983 | Obenaus et al. |
| 4,760,202 A | | 7/1988 | Dettmer et al. |
| 4,873,391 A | | 10/1989 | Inoue et al. |
| 5,475,183 A | | 12/1995 | Araki et al. |
| 5,672,782 A | * | 9/1997 | Hattori et al. ............ 568/899 |
| 5,716,895 A | * | 2/1998 | Sugi et al. ............ 502/24 |
| 5,756,604 A | * | 5/1998 | Nakaoka et al. ............ 526/69 |
| 2005/0043571 A1 | | 2/2005 | Fernandez et al. |
| 2005/0288534 A1 | | 12/2005 | Fernandez et al. |

FOREIGN PATENT DOCUMENTS

| | | | | |
|---|---|---|---|---|
| BE | 875433 | A1 | 7/1979 | |
| CN | 1176957 | A | 3/1998 | |
| CN | 1511814 | A | 7/2004 | |
| DE | 19635291 | A1 * | 6/1996 | ............ C08G 65/20 |
| EP | 0551022 | A1 | 7/1993 | |
| JP | 48-10121 | | 2/1973 | |
| JP | 54-160309 | A | 12/1979 | |
| JP | 55-7213 | A | 1/1980 | |
| JP | 55-51028 | A | 4/1980 | |
| JP | 55-62031 | A | 5/1980 | |
| JP | 55-64534 | A | 5/1980 | |
| JP | 56-2855 | A | 1/1981 | |
| JP | 56-10124 | A | 2/1981 | |
| JP | 58-39806 | A | 3/1983 | |
| JP | 58-116427 | A | 7/1983 | |
| JP | 63-41431 | A | 2/1988 | |
| JP | 4-300840 | A | 10/1992 | |
| JP | 8-143493 | A | 6/1996 | |
| JP | 11-193255 | A | 7/1999 | |
| JP | 2000-34242 | A | 2/2000 | |
| JP | 2000-43242 | A | 2/2000 | |
| JP | 2000-44497 | A | 2/2000 | |
| JP | 2000-44502 | A | 2/2000 | |
| KR | 10-2006-0049702 | A | 5/2006 | |

OTHER PUBLICATIONS

European Search Report, dated Apr. 2, 2009, for European Appln. No. 06822192.8.
J. L. Swecker et al., Journal of Catalysis, 121, 196-201 (1990).
English abstract of JP-54-135710-A issued Oct. 22, 1979.
Itani et al., "Manufacture of tertiary butanol—comprises reacting raw material containing olefin mixture with heteropoly acid containing molybdenum, tin or vanadium as coordination element, hydrating obtained product," Database WPI Week 200017 Thomson Scientific, Feb. 2, 2000, XP-002607609.

* cited by examiner

*Primary Examiner* — Johann R Richter
*Assistant Examiner* — Pancham Bakshi
(74) *Attorney, Agent, or Firm* — Birch, Stewart, Kolasch & Birch, LLP

(57) ABSTRACT

An object of the present invention is to provide, for the production of isobutene, a high-yielding, highly-selective, and long-term stable production process of isobutene from TBA. With respect to the production of TBA, an object of the present invention is to provide a TBA production process in which, through long-term stable maintenance of a high reaction activity, long-term continuous operation is enabled and the productivity is improved. The present invention discloses a process for producing isobutene that employs a dehydration temperature of from 200 to 450° C. in use of an alumina catalyst that contains a Na content of 0.6% by weight or less in terms of $NaO_2$ and a Na content of 0.4% by weight in terms of $NaO_2$, and has a specific surface area of from 200 to 600 $m^2/g$.

7 Claims, 3 Drawing Sheets

PROCESSES FOR PRODUCTION OF ISOBUTENE AND TERTIARY BUTANOL

TECHNICAL FIELD

The present invention relates to a high-yielding, highly-selective, and long-term stable production process of isobutene by dehydrating tertiary-butanol (abbreviated below as TBA) using an alumina catalyst that has special properties as a catalyst, and additionally relates to a high-yielding, highly-selective, and long-term stable continuous production process of TBA from water and an olefin mixture that contains isobutene and n-butene.

BACKGROUND ART

Isobutene is an important industrial starting material that in recent years has been in the spotlight as a starting material for isobutene polymers and methyl methacrylate (MMA). In addition, isobutene commonly exists in C4 olefin mixtures that generally contain n-butene or the like, and it therefore becomes necessary to separate isobutene from these C4 olefin mixtures.

In one process for producing isobutene from C4 olefin mixtures, n-butene-free isobutene is produced by the combination of a hydration reaction and a dehydration reaction. In other words, isobutene in the C4 olefin mixture is selectively hydrated and separated by recovery as TBA and the resulting TBA is dehydrated to obtain isobutene. Moreover, the TBA yielded by hydration and recovery/separation is also an important industrial raw material. In particular, demand for TBA has been growing in recent years since it can be used directly without dehydration as a starting material for MMA.

The olefin mixture as a starting material is mainly raffinate 1 (commonly known as "spent BB"), which is obtained by the removal of butadiene from the C4 fraction from the naphtha cracking process and has isobutene and n-butene as its main components. Alternatively, the olefin mixture as the starting material is a butene-containing C4 fraction obtained from the FCC cracking of heavy oil. Isobutene and n-butene are present in both starting materials, but are difficult to separate by distillation since the difference between their boiling points is small at no more than 1° C.; reactive separation processes have thus been devised in which the isobutene is selectively hydrated.

A packed fixed bed reaction using a strongly acidic ion-exchange resin is one process for carrying out the hydration reaction (for example, refer to Patent Documents 1, 2 and 3). This hydration reaction process provides an excellent separation from the catalyst since the catalyst is fixed; a drawback to this process, however, is a low reactivity due to a low contact efficiency. In order to enhance the reactivity and hydration reaction selectivity, a process has been disclosed in which the reactivity is improved by the use of a suitable solvent, circulating the reaction solution, and using an optimal circulation range (for example, refer to Patent Document 4). On the other hand, a process is known in which, for example, benzenesulfonic acid, is used as the catalyst in a homogeneous hydration reaction (for example, refer to Patent Document 5). Processes are also known in which contact is effected with an aqueous heteropolyacid solution as a catalyst (for example, refer to Patent Documents 6, 7, 8 and 9). Problems requiring attention still remain with fixed bed reactions that use, e.g., an acidic ion-exchange resin, for example, as follows: a majority of the product exiting the reactor must be circulated, water is not to be mixed with the hydrocarbon that is the reaction starting material, and an organic acid and/or TBA (the reaction product) must be added as solvent in order to raise the wettability on the solid ion-exchange resin and thereby raise the contact efficiency. While the heteropolyacid process is an excellent process that provides a high reactivity and also a high selectivity for isobutene, the process as a whole is not entirely free of problems and some issues remain; improvements thereto have been carried out (refer, for example, to Patent Documents 10, 11 and 12).

However, for each of these production processes the problem still remains of being able to continue production on a long-term stable basis. Timewise changes occur, for example, as follows: although each catalyst exhibits an excellent initial activity, the catalytic activity undergoes a gentle but gradual decline over the timeframe of a year; the separation capacity of the catalyst separator declines; and the separation performance of the distillation column declines. One solution for this is to keep the continuous reaction running by discarding a portion of the catalyst that has undergone long-term use in the reaction and making this up with fresh catalyst. Within the context of the green chemistry movement seen in recent years, reducing the amount of this discard then becomes an issue.

Processes that are carried out in a homogeneous system using a strong acid, for example, sulfuric acid, have long been in general use for dehydration reactions. However, these processes are undesirable as industrial production processes because the high corrosivity due to the use of a strong acid requires a corrosion-resistant production apparatus and because it is difficult to treat the spent sulfuric acid discharged after the dehydration reaction. Several processes have been introduced in recent years that solve these problems by carrying out the dehydration reaction in a heterogeneous system using a sulfonic acid group-containing strongly acidic ion-exchange resin as the catalyst. In one process disclosed in this sphere, TBA is dehydrated at 80 to 150° C. on a fixed bed that uses an ion-exchange resin. However, when the reaction temperature in this process is 120° C. or below, due to the fact that the TBA and isobutene and water are in an equilibrium relationship, the post-reaction compositional proportion of the water rises and the reaction rate declines. This results in a low one-pass conversion, making it necessary to recycle large amounts of TBA and water and causing a complex production process. When the reaction is carried out at temperatures above 120° C., isobutene oligomerization, a secondary reaction, proceeds and the yield is reduced (for example, refer to Patent Document 13).

On the other hand, numerous processes are also known for the gas-phase production of isobutene using a solid acid catalyst. Since the dehydration reaction of alcohols is a highly endothermic reaction, it is generally carried out at high temperatures, i.e., 250° C. and above, in the gas phase, as is done in Patent Document 14. A characteristic feature of this dehydration reaction is the production of, for example, diisobutene, by the oligomerization of the isobutene product, and the reaction is preferably run at higher temperatures in order to inhibit this oligomerization. However, raising the temperature results in an acceleration of carbon deposition on the surface of the catalyst, causing a timewise decline in the activity of the catalyst and having a negative influence on long-term stable industrial production.

In the production of olefin by alcohol dehydration, the development of a catalyst that can maintain its catalytic activity long term is very significant for gas-phase reactions that use a solid acid catalyst, and several processes have been quite recently proposed. One such process that has been proposed is the use of γ-alumina as the catalyst for producing lower olefin by the dehydration of $C_2$ to $C_4$ lower alcohol (for example, refer to Patent Document 15). However, according to the disclosures in Patent Document 15, isobutanol is used as the starting material for the isobutene production processes in the examples, and what the results would be for the use of TBA as the starting material cannot be predicted. In addition, high pressures are required in order to achieve the object and the isobutene yield in the examples is also not satisfactory.

Thus, as described above, problems still remain with the heretofore known processes, both with the processes carried out at relatively low temperatures in the liquid phase and the processes carried out at high temperatures in the gas phase. With regard to processes using a solid acid catalyst in the gas phase, the current situation, in accordance with the preceding description in connection with Patent Document 15, is that there has been no report of a catalyst capable of long-term maintenance of its catalytic activity in the production of isobutene from TBA in the gas phase using a solid acid catalyst.

[Patent Document 1] Japanese Patent Application Laid-open No. S56-10124
[Patent Document 2] Japanese Patent Publication No. S56-2855
[Patent Document 3] Japanese Patent Application Laid-open No. S55-64534
[Patent Document 4] Japanese Patent Application Laid-open No. H11-193255
[Patent Document 5] Japanese Patent Application Laid-open No. S55-51028
[Patent Document 6] Japanese Patent Application Laid-open No. S54-160309
[Patent Document 7] Japanese Patent Application Laid-open No. S55-7213
[Patent Document 8] Japanese Patent Application Laid-open No. S55-62031
[Patent Document 9] Japanese Patent Publication No. S58-39806
[Patent Document 10] Japanese Patent Application Laid-open No. 2000-44497
[Patent Document 11] Japanese Patent Application Laid-open No. 2000-43242
[Patent Document 12] Japanese Patent Application Laid-open No. 2000-44502
[Patent Document 13] Japanese Patent Application Laid-open No. S58-116427
[Patent Document 14] Japanese Patent Publication No. S48-10121
[Patent Document 15] Japanese Patent Application Laid-open No. H4-300840

DISCLOSURE OF INVENTION

Problems to be Solved by the Invention

An object of the present invention is to provide a high-yield, high-selectivity, and long-term stable process for producing isobutene from TBA using an alumina catalyst. Another object of the present invention is to provide a continuous, long-term stable process for producing TBA from a hydrocarbon mixture containing isobutene and n-butene by selectively hydrating the isobutene using an acid as catalyst.

Means for Solving the Problems

To develop a process for producing isobutene from TBA in a cost-effective manner, the present inventors carried out intensive investigations focusing on the use of a solid acid catalyst in the gas phase. Carbon deposition on the catalyst surface under dehydration reaction conditions, which causes a timewise decline in catalytic activity, is known to depend on the acid strength of the solid acid, and it is also known that a higher acid strength results in a stronger promotion of carbon deposition through the occurrence of cyclization, dehydrogenation, hydrogen transfer reactions, and the like by the isobutene product. The solid acids that are generally strongly acidic, such as silica-alumina, while exhibiting a high initial activity, have evidenced a substantial timewise decline in activity due to carbon deposition. Specific investigations were therefore carried out among alumina catalysts, which are generally weakly acidic, using catalysts having different specific surface areas, different pore volumes, and different impurity contents, e.g., Na and the like, in the catalyst, and it was unexpectedly discovered as a result that carbon deposition does not occur on the long term and a high activity is therefore maintained and that the selectivity for isobutene is also high.

Moreover, one problem that occurs when TBA is produced by long-term operations is that, due to phenomena in which a gentle decline in reaction activity, a deterioration in the catalyst separation characteristics, and a decline in distillation column separation capacity decline with elapsed reaction time, the reactivity and operability must be restored by intermittently stopping the plant and replacing a portion of the catalyst. In order to realize a long-term stable operation, the present inventors carried out investigations in order to thoroughly analyze these phenomena and to solve them. As a result, the present invention was achieved based on the knowledge that, in TBA production, accumulating impurity is the cause of the decline in catalytic activity, the deterioration in catalyst separation, and the decline in distillation column separation performance.

That is, according to the first aspect of the present invention, there is provided:

[1] a process for producing isobutene using tert-butanol as a starting material, comprising:
carrying out a dehydration reaction in a gas phase at a reaction temperature of from 200 to 450° C. using an alumina catalyst which has a Na content in a range of from 0.1 to 0.6% by weight in terms of $Na_2O$ and a Si content of not more than 0.4% by weight in terms of $SiO_2$, and which has a specific surface area of from 200 to 600 $m^2/g$;

[2] the process for producing isobutene according to item [1], wherein the alumina catalyst has a total pore volume in the catalyst of from 0.1 to 0.5 cc/g and has a pore volume of pores having a pore radius of at least 70 Å, the pore volume being at least 60% of the total pore volume;

[3] the process for producing isobutene according to item [1] or [2], wherein the tert-butanol is produced by a process that produces tert-butanol from a hydrocarbon mixture containing isobutene and n-butene by selectively hydrating the isobutene using an aqueous catalyst solution containing water and a heteropolyacid catalyst.

Further, according to the second aspect of the present invention, there is provided:

[4] a process for continuously producing tert-butanol from a hydrocarbon mixture containing isobutene and n-butanol by selectively hydrating the isobutene using an aqueous catalyst solution comprising water and a catalyst, the process comprising the steps of:
recycling at least one selected from the hydrocarbon mixture, the catalyst, and the tert-butanol using a recycle system that circulates the at least one; and
removing a portion of accumulating impurity from the recycle system;

[5] the production process according to item [4], wherein a porous adsorbent and/or an ion-exchange resin is used at the step of removing the accumulating impurity;
[6] the production process according to item [4] or [5], wherein a pore radius of the porous adsorbent is in a range of 0.5 to 500 nm;
[7] the production process according to any one of items [4] to [6], wherein the catalyst is a strong acid or a strong acid salt that exhibits $-5.6 \geq H_0$ where $H_0$ is the Hammett acidity function;
[8] the production process according to any one of items [4] to [7], wherein the catalyst is a heteropolyacid;
[9] the production process according to item [8], wherein the heteropolyacid is selected from the group consisting of phosphomolybdic acid, phosphomolybdovanadic acid, phosphotungstic acid, phosphotungstovanadic acid, silicotungstic acid, and salts thereof, wherein a single heteropolyacid or a mixture of two or more heteropolyacids is used;
[10] the production process according to item [5], wherein the ion-exchange resin is a cation-exchange resin;
[11] the production process according to any one of items [4] to [10], further comprising: reacting the aqueous catalyst solution and the hydrocarbon mixture while feeding the aqueous catalyst solution and the hydrocarbon mixture in a counterflow manner;
[12] the production process according to any one of items [4] to [11], further comprising: continuously or discontinuously adding an oxidizing agent.

Furthermore, according to the third aspect of the present invention, there is provide:
[13] an apparatus for continuously producing tert-butanol, comprising:
a at least one stirring tank-type reactor;
a distillation column connected to the stirring tank-type reactor;
a separator which is connected to the stirring tank-type reactor and/or the distillation column and which removes an impurity; and
a bottom liquid conduit that communicates with the separator, the stirring tank-type reactor and/or the distillation column;
[14] the apparatus for continuously producing tert-butanol according to item [13], wherein the stirring tank-type reactor comprises a catalyst separator;
[15] the apparatus for continuously producing tert-butanol according to item [14], wherein the separator communicates with the catalyst separator;
[16] the apparatus for continuously producing tert-butanol according to any one of items [13] to [15], wherein the separator comprises a column of adsorbent and/or a column of ion-exchange resin;
[17] the apparatus for continuously producing tert-butanol according to any one of items [13] to [16], wherein the stirring tank-type reactor is a counterflow-type reactor that reacts the aqueous catalyst solution and the hydrocarbon mixture as the starting material while the aqueous catalyst solution and the hydrocarbon mixture as the starting material are fed in a counterflow manner;
[18] the apparatus for continuously producing tert-butanol according to any one of items [13] to [17], wherein a material in the continuous production apparatus at a location in a contact with the catalyst, comprises a stainless steel that at least comprises a Cr content of from 17 to 21%, a Ni content of from 8 to 14%, and a C content of no more than 0.10%,
[19] the apparatus for continuously producing tert-butanol according to item [18], wherein the catalyst is a heteropolyacid.

Advantageous Effects of the Invention

With respect to the production of isobutene, the isobutene production process according to the present invention can produce isobutene from tert-butanol at high yields and high selectivities in a stable manner on a long-term basis. With respect to the production of tert-butanol, the tert-butanol production process is provided in which, through long-term stable maintenance of a high reaction activity, long-term continuous operation is made possible and the productivity is improved. Moreover, catalyst losses and the production losses associated with operating stoppages can be substantially reduced and waste reduction and energy savings can be realized.

BEST MODE FOR CARRYING OUT THE INVENTION

The present invention is further described in detail in the following through examples and comparative examples of the present invention; however, these are provided for purposes of illustration and the present invention is not limited to the specific examples that follow. A person skilled in the art will be able to implement the present invention by introducing various modifications into the examples provided below; these modifications are encompassed by the scope of the patent claims of this application.

One aspect of the present invention relates to a process for producing isobutene by a dehydration reaction in the gas phase using tert-butanol (referred to below as TBA) as a starting material.

The catalyst used in the isobutene production process according to the present invention is alumina whose main component is the γ-crystalline structure. A Na content in the alumina catalyst is in a range of from 0.1 to 0.6% by weight, preferably from 0.1 to 0.5% by weight, and more preferably 0.1 to 0.4% by weight in terms of $Na_2O$. The Si content in the alumina catalyst is in a range of no more than 0.4% by weight, preferably no more than 0.3% by weight, and more preferably no more than 0.2% by weight in terms of $Si_2O$. The specific surface area is from 200 to 600 $m^2/g$, preferably from 250 to 600 $m^2/g$, and more preferably from 300 to 600 $m^2/g$.

The reason why the alumina catalyst used for isobutene production is particularly effective in the dehydration reaction is presumed to be the presence of an acidity optimal for dehydration reaction activity. As the amount of Na present in the alumina catalyst rises, the acid sites on the catalyst surface are neutralized and the dehydration reaction yield undergoes a substantial decline. In contrast to this, when $SiO_2$ is present in the alumina catalyst as an impurity, strong acid sites originating with Si—O—Al appear accompanying an increasing Si content, which reduces the dehydration reaction yield and accelerates carbon deposition. For this reason, smaller Na and Si contents in the alumina catalyst are increasingly advantageous. However, when $SiO_2$ is present in the alumina catalyst, even at quite low levels, Na becomes necessary at some level in order to neutralize the strong acid sites originating with the Si. Since it is generally impractical to remove the Si completely from the alumina catalyst used in the dehydration reaction, it then becomes important that the minimum Na content necessary to maintain the acidity of the catalyst surface in an optimal state be present. On the other hand, it could also be contemplated that in the case of an alumina catalyst containing a certain level of $SiO_2$, an optimal acidity could be obtained if the strong acid sites present were neutralized by Na. However, when the Na and Si at the catalyst surface are increased in this case, their distribution becomes non-uniform, and, since acid sites active in the dehydration reaction then end up being neutralized while strong acid sites remain present, the dehydration reaction yield undergoes a substantial decline.

The magnitude of the specific surface area of the alumina catalyst used for isobutene production not only contributes to the dehydration reaction activity, but also has the effect of delaying the timewise decline in catalytic activity due to carbon deposition, and as a consequence the specific surface area is from 200 to 600 m$^2$/g, preferably from 250 to 600 m$^2$/g, and more preferably from 300 to 600 m$^2$/g. The specific surface area is preferably no greater than 600 m$^2$/g for the following reason: small-radius pores make up a small proportion of the total pore volume in an alumina catalyst having a specific surface area no greater than 600 m$^2$/g, which works against carbon deposition-induced pore clogging and thereby slows the timewise decline in catalytic activity.

The alumina catalyst used for isobutene production is preferably an alumina catalyst that has the properties described above as well as also having the following properties in combination therewith: a total pore volume in the alumina catalyst of from 0.1 to 0.5 cc/g and a pore volume for pores having a pore radius of at least 70 Å that is at least 60% of the total pore volume. A high dehydration reaction yield and little timewise decline in catalytic activity are obtained when the alumina catalyst has a total pore volume in the aforementioned range and satisfies the aforementioned range for the pore volume attributable to pores with a pore radius of at least 70 Å.

With regard to the method for producing the alumina, alumina produced by known methods can be used as long as the properties of the alumina catalyst used for isobutene production are in the ranges described above. For example, the alumina can be readily produced by thermal decomposition, precipitation, deposition, or mixing/kneading, or by combinations of these methods. In this case, the alumina precursor can be, for example, a nitrate, acetate, alkoxide, sulfate, chloride, alkali aluminate, alum and the like, that produces alumina or alumina hydrate by heating or hydrolysis. Examples of the alkali used for hydrolysis include alkali hydroxides, alkali carbonates, aqueous ammonias, ammonium carbonates and the like, the alkali lacking a sodium fraction being preferred.

The shape of the alumina catalyst used for isobutene production is not particularly limited, and a powder, granule, sphere, cylinder, ring, and the like may be used; in practice the shape is determined based on a consideration of the pressure losses in the reactor. A sphere with a diameter of 0.5 to 20 mm, a cylinder with a diameter and height of 2 to 20 mm, or a ring with an outer diameter of 4 to 20 mm, an inner diameter of 2 to 16 mm, and a height of 2 to 20 mm is typically used.

The method of forming the alumina catalyst used for isobutene production is not particularly limited. When the formation of a spherical configuration is sought, the catalyst forming method is typically tumbling granulation, marumerizing method, fluid bed granulation and the like; when the formation of a cylindrical or ring configuration is sought, extrusion molding or tableting is typically used; however, any method may be used. Pretreatment of the catalyst is not specifically required, but a pretreatment, for example, calcination and the like, may be carried out.

The reaction conditions for dehydration of TBA as the starting material in the isobutene production process according to the present invention are described in the following. Specifically, the reaction temperature is from 200 to 450° C., preferably from 250 to 420° C., and more preferably from 300 to 400° C. Dehydration temperatures in this range are preferred from the standpoints of the dehydration reaction yield and the inhibition of carbon deposition.

The feed rate of the starting material to the reactor is from 0.1 to 10 hr$^{-1}$ and preferably from 0.5 to 5 hr$^{-1}$ as the liquid hourly space velocity (LHSV) of TBA as the starting material. Liquid hourly space velocities in this range are preferred from the standpoints of the economics, dehydration reaction yield, and inhibition of carbon deposition. The reaction pressure is not particularly limited, and reduced pressure, ambient pressure, and applied pressures may be used; however the applied pressures are advantageous from the standpoint of enabling condensation with the coolants typically used in the industry and from the standpoint of enabling a reduction in the size of the reactor and a reduction in the amount of the catalyst.

The TBA vapor as the starting material is generally supplied in combination with an inert gas such as a steam and/or nitrogen; however, operation and production are also possible according to the process of the present invention using the pass-through of only TBA vapor. This is due to the low occurrence of secondary reactions in the isobutene production process according to the present invention and due to the low carbon deposition that is also a characteristic feature of the isobutene production process according to the present invention.

A continuous reaction is preferred for the reaction mode for the isobutene production process according to the present invention, while a fixed bed is preferred for the reactor configuration.

TBA as the starting material used in the isobutene production process according to the present invention need not be pure, and TBA as the starting material can be used that contains small amounts of organics that do not undergo chemical reaction under the reaction conditions. However, organics that might cause carbon deposition are preferably absent to the maximum extent possible. TBA as the starting material is more preferably TBA that has been produced from a hydrocarbon mixture containing isobutene and n-butene by the selective hydration of the isobutene using an aqueous catalyst solution containing water and a heteropolyacid catalyst. As a result of investigations using TBAs produced by various different methods, the inventors found that TBA produced by hydration over heteropolyacid has the least amount of impurities (e.g., diisobutene, oxygenated compounds, and the like) and the least carbon deposition. The high selectivity of the hydration reaction by heteropolyacid is thought to be one cause of this. With respect, on the other hand, to TBA produced by other methods, for example, TBA produced as a secondary product during the production of propylene oxide contains large amounts of oxygenated compounds, such as ketones and the like. TBA produced by hydration over ion-exchange resin contains esters between the butenes and the organic acid added in order to raise the contact efficiency. The TBA produced without using organic acid, because it contains substantial diisobutene, presumably has the potential to promote carbon deposition. Water-containing TBA can also be used, and the use of TBA, as the starting material, containing water at a certain level is preferred from the standpoint of inhibiting carbon deposition. When water-containing TBA can be used as the starting material, this offers the economic advantage of making it unnecessary to implement a purification process in which the water, which forms an azeotrope with TBA, is removed; moreover, such TBA resists freezing at low temperatures and is thus easy to handle. With regard to the water concentration, TBA produced using heteropolyacid for the catalyst is a more preferred starting material because it has a stable and defined water concentration.

The process for producing TBA that is another aspect of the present invention is described in the following. In relation to the TBA production process according to the present invention, it was ascertained that accumulating impurity causes the decline in catalytic activity, the deterioration in catalyst separation, and the decline in distillation column separation performance in the continuous production of TBA from a hydrocarbon mixture containing isobutene and n-butene by the selective hydration of isobutene using an aqueous catalyst solution containing water and catalyst. The TBA production process according to the present invention therefore provides a stable continuous process for producing TBA, through the provision of a novel technical concept, i.e., a step of managing the accumulating impurity such that it does not exceed a prescribed concentration through the use of a recycle system that circulates at least one selection from the TBA, aqueous catalyst solution, and hydrocarbon mixture containing isobutene and n-butene.

In another aspect of the present invention, there is provided, as a reaction system for efficiently securing and maintaining TBA production, a continuous tert-butanol production apparatus for TBA production according to the present invention. The continuous ter-butanol production apparatus according to the present invention comprises at least one stirring tank-type reactor; a distillation column that is connected to the stirring tank-type reactor; a separator that is connected to the stirring tank-type reactor and/or the distillation column and that removes impurity; and a bottom liquid conduit that communicates with the separator, stirring tank-type reactor, and/or distillation column. In a preferred aspect of the continuous production apparatus according to the present invention, the stirring tank-type reactor is provided with a catalyst separator and this catalyst separator is also connected to the aforementioned separator. In another preferred aspect of the continuous production apparatus according to the present invention, the aforementioned separator is provided with a column of adsorbent and/or a column of ion-exchange resin. In relation to the production of TBA, the aforementioned stirring tank-type reactor in a preferred aspect of the continuous production apparatus according to the present invention is a counterflow-type reactor in which the aqueous catalyst solution and the hydrocarbon mixture as the starting material are reacted while being fed in a counterflow manner. A high productivity can be realized by carrying out the reaction while feeding the aqueous catalyst solution and the hydrocarbon mixture as the starting material in a counterflow manner. In addition, a diminished activity can also be regenerated by the addition of an oxidizing agent. Proceeding in the manner laid out in the foregoing, a recycle system for the starting material, product, or catalyst can be established via the separator, as described below, in the continuous TBA production apparatus according to the present invention.

The impurity that accumulates due to the reaction conditions under which TBA is produced from the hydrocarbon mixture containing isobutene and n-butene by the selective hydration of the isobutene using the aqueous catalyst solution containing water and catalyst, is estimated to be formed in many cases from a plurality of substances, although a single impurity is also a possibility. For example, in one of these cases, the present inventors found that the accumulation in the reaction system of reactor material as metal ion yielded by dissolution by, for example, corrosion, is also a factor in the decline in catalytic activity. The acidic catalyst material was presumed to be the cause, and, through a broad investigation into metal materials that could substantially reduce corrosion and also through experiments, a phenomenon was discovered that could not be predicted from the conventional corrosion resistance concept for stainless steel. That is, in TBA production in the present invention, the production of impurity in the reaction system can be inhibited as much as possible and a trace amount of accumulating impurity that is produced is concentrated in the recycle system and effectively removed. While it might normally be concluded that impurity elimination is preferably carried out at a site where the impurity is produced or exists, when this was actually attempted it was very difficult to effectively eliminate trace amounts of impurity. However, even in those instances where elimination is problematic due to the trace levels, concentration of the accumulating impurity at the recycle system according to the present invention dramatically facilitates the separation efficiency and makes possible an effective separation with simple equipment.

The removal step in the TBA production process according to the present invention is carried out in at least one recycle system, vide infra, for the accumulating impurity, and the step of removing the accumulating impurity can be carried out at a suitable location in accordance with differences, for example, in the reaction procedure. When a large amount of accumulating impurity is present in the aqueous catalyst solution, the removal step can be conducted in the catalyst recycle system. Moreover, when a large amount of accumulating impurity is present in the unreacted starting material system, the removal step can be carried out in the recycle system for the unreacted starting material system. When a large amount of accumulating impurity is present in a system that circulates a portion of the product, the removal step can be carried out in a recycle system for the product, and the removal step is preferably carried out in a recycle system at an effective location in correspondence to the process. In addition, the accumulating impurity can also be removed in all of the recycle systems, i.e., for the catalyst, starting material, and product, in the TBA production process according to the present invention.

The step of removing accumulating impurity in the TBA production process according to the present invention is described below using the example of a system that uses for an aqueous heteropolyacid solution as the strongly acidic catalyst used in the TBA production process according to the present invention.

(In the Catalyst Recycle System)

The anion in the heteropolyacid catalyst has a diameter of approximately 1 nm and is thus a larger anion than in nitric acid, hydrochloric acid, and sulfuric acid, which are common mineral acids. This has the result of increasing the protonic acid strength in comparison to the other mineral acids. At the same proton concentration, a higher reaction activity is exhibited in the isobutene hydration reaction than is exhibited by the common mineral acids such as nitric acid. In addition, the interaction between the large anion and isobutene is assumed to be stronger than for n-butene, which is thought to elicit a higher selectivity in the hydration reaction. Moreover, heteropolyacid is stable in the reaction temperature range of about 100° C., and this also offers a lifespan advantage over ion-exchange resins, which are subject to thermal deterioration. Thus, heteropolyacid is superior to ion-exchange resin as a catalyst. However, when in recent years the continuous reaction has been continued for an extended period of time on the order of a year, the problem has appeared of a decline, although gentle, in the reaction activity. As a result of detailed investigations of this deterioration and its causes, the present inventors discovered the solution described below for the TBA production process according to the present invention.

That is, impurity accumulation was found as a result of an analysis of an aqueous heteropolyacid solution from a recycle system, which had been used in a long-term reaction and had undergone a decline in catalytic activity. In view of this, for example, the accumulating impurity can be removed by adsorptive separation, for example, from a location that carries out recycle circulation of a portion of the aqueous catalyst solution at a bottom of the distillation column that distillatively separates the dissolved TBA. Furthermore, it was discovered that the catalyst separation characteristics, the operability of the distillation column, and the activity could be recovered by the addition of an oxidizing agent. While the mechanisms of the activity decline and the recovery have not been elucidated in their entirety, it is thought that, during reaction operations that reach into the long term, the trace impurity that is produced remains in and accumulates in the recycle system, reaching a high concentration, and, for example, a foaming phenomenon is evoked in the operation of the distillation column that causes a deterioration in separation behavior in the catalyst separation step, causing a deterioration in the separation characteristics. It is also hypothesized that the reaction of isobutene is inhibited due to adsorption to or coordination with the heteropolyacid catalyst. As one consideration in this regard, the iron ion, which based on an analysis of the aqueous catalyst solution was not observed during the initial period of the reaction, underwent a clear increase as the reaction time increased. That is, metal ions, such as iron, that elute from the reactor and the pipe material are presumed to be an accumulating impurity. It is thought that the production of the iron ion and the like is caused by corrosion from the material making up the apparatus, for example, the reactor. As a result of investigations into methods of removing these metal ions, it was discovered that the metal ions are almost entirely removed by selective absorption on ion-exchange resin.

Active carbons can also be used for the adsorptive removal of metal ions. However, for the selective removal of metal ions, the use of a selection from the ion-exchange resins is preferred for metal ion removal. Specific examples thereof include cation-exchange resins having the sulfonic group or carboxyl group, such as styrenic gel types, styrenic MR types, methacrylic acid MR types, acrylic acid MR types, acrylic acid gel types, and the like. A suitable selection from the chelate resin or H(acid)-form is more preferred for use than the Na-form.

(In the Starting Material Recycle System)

The butenes in the hydrocarbon mixture as the starting material that contains isobutene and n-butene, because they have a reactive functional group, i.e., the vinyl group, are presumed to produce, for example, by a polymerization reaction in some form, accumulating high-boiling organic compounds.

A detailed description is given of a process that solves the deterioration in the separation of the catalyst phase (aqueous phase) from the hydrocarbon phase (oil phase), for which the cause was inferred to be the accumulating high-boiling organic compounds. It was hypothesized that the phenomenon in which the aqueous catalyst solution phase and the hydrocarbon phase, i.e., the water phase and oil phase, deteriorate occurs because a component capable of emulsifying oil and water, that is, an accumulating impurity that has a surfactant function, is produced in trace amounts in the system and accumulates with elapsed time. As a result of in-depth research, this impurity was successfully subjected to adsorptive separation when certain adsorbents were used. An analysis of this impurity was able to confirm that it had surface-active behavior. Moreover, when the impurity was extracted and added to fresh aqueous catalyst solution and hydrocarbon mixture, the phenomenon of deterioration in the separation interface was clearly reproduced.

That is, impurity that accumulates in the recycle system is the causative substance for the deterioration in the catalyst separation interface and the causative substance with regard to distillation column separation (foaming). Moreover, it was also ascertained, based on analyses using NMR, MS, IR, and the like, that this is impurity that has a functionality similar to that of a surfactant and presumably has an organic molecule moiety and an anion.

(In the Product Recycle System)

The relationship between an increased concentration of accumulating impurity and the occurrence of deterioration could also be experimentally verified for the deterioration in the separation performance at the distillation column. It has been discovered that when TBA, which is the product of the isobutene hydration reaction, is present in a certain concentration range in the aqueous catalyst solution, it has the ability to extinguish the foaming phenomenon that occurs in the distillation column, as shown in Japanese Patent Application Laid-open No. 2000-44502. Since alcohols are used as defoaming agents that inhibit foaming, TBA, which is the intended product of the reaction, is also thought to function as a defoaming agent.

However, it was discovered in the TBA production process according to the present invention that even when TBA is not present the deterioration in catalyst separation and the deterioration in the operability of the distillation column can be inhibited by removing the accumulating impurity. That is, it is from 10.0 to 0.1% by weight, preferably from 5.0 to 0.1% by weight, and more preferably from 3.0 to 0.1% by weight as a concentration of the surface-active accumulating impurity in the aqueous catalyst solution. While control to these low levels is preferred, this increases the load, for example, large amounts of the adsorbent used for removal then become necessary. Accordingly, an optimal concentration level can be established in view of, for example the TBA concentration, and as function of the separation status and the operating conditions. As a result of intensive investigations into functional materials that would effectively remove the accumulating impurity considered to be the foam-causing material, it was discovered that a simple dependence does not obtain between the absorbent's surface area and the adsorption effects and that for one of the adsorption effects the pore diameter is an important factor. Specifically, a porous adsorbent is preferred. Examples of the adsorbent include inorganic porous materials such as silica, alumina, active carbon, zeolites, and mesoporous zeolites, e.g., large pore diameter MCM-41; crosslinked synthetic organic polymers lacking ion-exchange groups and derived from styrene-divinylbenzene or methacrylate ester and ethylene glycol dimethacrylate; chitosan resin; and the like. It is an adsorbent having a porosity of a size wherein the pore radius is in a range of from 0.5 to 500 nm, and preferably is a porous material having pores with a radius of from 1 to 250 nm and more from 2 to 50 nm. From the material perspective, an oleophilic material is more preferred than a hydrophilic material, and preferred materials are organic-modified silica gel (e.g., modified with a silane coupling agent), organic-modified alumina, mesoporous material such as organic-modified MCM-41, and more preferably synthetic resin-type materials.

In this manner, the accumulating impurity is concentrated and removed in the particular recycle system in the TBA production process according to the present invention by using a recycle system for the catalyst, starting material, or product and by disposing a separator, e.g., of adsorbent and/or ion-exchange resin, in the recycle system. This concentration and removal makes possible the long-term stable maintenance of the reaction activity of the catalyst and the realization of a continuous TBA production.

A material that exhibits acidity can be used as the catalyst used in the TBS production process according to the present invention; however, viewed from the perspective of the reaction rate, use can be made of strongly acidic materials for which the Hammett acidity function $H_0$ is represented by $-5.6 \geq H_0$. Specific examples of the strongly acidic materials include $SiO_2$—$Al_2O_3$, $SiO_2$—$ZrO_2$, $SiO_2$—$BeO$, $SiO_2$—$Y_2O_3$, $SiO_2$—$La_2O_3$, $Al_2O_3$—$ZrO_2$, $TiO_2$—$ZrO_2$, H—Y zeolite, H—ZSM-5, at least 80% $H_2SO_4$, Nafion-H, strongly acidic cation-exchange resins, para-toluenesulfonic acid, heteropolyacid, and the like, and a selection therefrom can be used as the acid catalyst.

As specific examples of the heteropolyacid used in the TBA production process according to the present invention, use can be made of acids such as $H_3PMo_{12}O_{40}$, $H_6P_2Mo_{18}O_{62}$, $H_9AlMoO_{24}$, $H_3AsMo_{12}O_{40}$, $HBCeMo_{12}O_{42}$, $HgGaMoO_{24}$, $H_5IMo_{12}O_{40}$, $H_4SiMo_{12}O_{40}$, $H_4GeMoO_{12}O_{40}$, $H_4PVMo_{11}O_{40}$, $H_5PV_2Mo_{10}O_{40}$, $H_5BW_{12}O_{40}$, $H_4PW_{11}AlO_{40}$, $H_3PW_{12}O_{40}$, $H_5AlW_{12}O_{40}$, $H_6SiV_2W_{10}O_{40}$, $H_5SiVW_{11}O_{40}$, $H_4SiW_{12}O_{40}$, $H_5GaW_{12}O_{40}$, $H_9NdW_{18}O_{36}$, $H_9CeW_{18}O_{36}$, and $H_6P_2W_{18}O_{62}$ and salts such as $H_3NaSiW_{12}O_{40}$ and $H_3KSiW_{12}O_{40}$, phosphomolybdic acid ($H_3PMo_{12}O_{40}$), $H_4PVMo_{11}O_{40}$, phosphotungstic acid ($H_3PW_{12}O_{40}$), phosphotungstic acid ($H_4PVW_{11}O_{40}$), and silicotungstic acid ($H_4SiW_{12}O_{40}$) being preferred for their reactivity.

With regard to the material of the apparatus used in the TBA production process according to the present invention, examples of the locations in contact with the acidic aqueous catalyst solution include reaction vessels, stirring blades, diaphragms, packing, decanters, settlers, distillation columns, distillation column trays, pipes, flanges, measurement device members, connection members such as joints, and the like. Materials such as iron e.g., carbon steel, copper, brass, aluminum, and the like, would be strongly corroded when used as these members, making such materials undesirable. Stainless steel is the preferred material for members in contact with the heteropolyacid catalyst, and stainless steel can be broadly used. More preferably, stainless steel having an alloy system of iron, chromium, and nickel is a material that exhibits excellent corrosion properties. As a material with a well-adapted corrosion resistance, austenitic stainless steel containing a Cr content of from 17 to 21%, a Ni content of from 8 to 14%, and a C content of no more than 0.10% is even more preferred at locations in contact with the heteropolyacid. Using the Japanese Industrial Standards, examples of the stainless steel include SUS304, 304L, 305, 305L, 308, 316, 316J, 316L, 317, 317L, and the like, SUS304 being more preferred. With regard to the mechanism by which these materials specifically manifest corrosion resistance, the present inventors presume that the constituent elements of these materials and the heteropolyacid undergo specific reactions with each other at a surface of the material to form a stabilized passive layer, which in turn can inhibit the development of corrosion.

It was discovered with respect to the TBA production process according to the present invention that the addition of an oxidizing agent results in the recovery of the catalytic activity and also attenuates the degree of coloration of the somewhat colored aqueous catalyst solution. This is believed to be due to the following: oxidation of catalyst that has been reduced through oxidation, and oxidative degradation and hence removal of impurity that was causing inhibition of the reaction. With regard to the oxidizing agent, an improvement in the activity is seen with an oxidation method that uses air or oxygen; however, this requires a somewhat lengthy period of time. Ozone and electrochemical oxidation methods can also be used as the oxidizing agent. The oxidizing agent preferably has a high oxidizing power, such as hydrogen peroxide. As an index of the oxidizing power, the oxidizing power is preferably equivalent to that of hydrogen peroxide, and a more preferred oxidizing agent, such as hydrogen peroxide, occurs as water after the reaction, and does not have a significant influence on the hydration reaction. The amount and frequency of oxidizing agent addition cannot be determined according to a fixed rule because they vary as a function of, inter alia, the type of oxidizing agent, the extent of the decline in activity due to the length of time the catalyst has been in use, and the amount of accumulating impurity that is also present. However, in the case, for example, of the use of hydrogen peroxide as the oxidizing agent, even when added in excess the hydrogen peroxide ends up degrading with elapsed time and thus its addition in some excess is unproblematic; hydrogen peroxide is selected as a preferred oxidizing agent also from this perspective. However, the addition of an excess of hydrogen peroxide, being without benefit, is undesirable from an economic standpoint. Accordingly, the continuous or discontinuous addition of hydrogen peroxide at from 0.01 to 5000 ppm/h, preferably from 0.1 to 3000 ppm/h, and more preferably from 1 to 1000 ppm/h, in each case with reference to the aqueous catalyst solution, provides exemplary instances of the use of hydrogen peroxide as general criteria for addition, although the addition is determined at any particular time point based on the actual operating results. The temperature in the event of addition can be selected from the temperature range from room temperature to about 100° C. Since higher temperatures generally result in a faster oxidation reaction rate but also increasingly facilitate degradation of the hydrogen peroxide itself, it is preferable to select a temperature of from 30 to 80° C., more preferably from 40 to 80° C. With regard to the location of oxidizing agent addition, for the most part the location is preferred where the aqueous phase that forms from the catalyst and water is formed, and a site or location from which hydrocarbon, e.g., olefin and the like, is absent to the greatest extent possible is more preferred.

EXAMPLES

The present invention is specifically described in the following by examples and comparative examples, but these in no way limit the scope of the present invention. The measurement methods used in the examples of the isobutene production process according to the present invention were as follows.

(1) Measurement of a Na content and Si content in the alumina catalysts

Analysis was carried out using an RIX1000 (Rigaku) by X-ray fluorescence analysis using reference samples.

(2) Measurement of the specific surface area of the alumina catalysts

The specific surface area was measured by the nitrogen adsorption method using a Gemini 2360 (Shimadzu).

(3) Measurement of the pore volume and pore distribution in the alumina catalysts The pore volume and pore distribution were measured by mercury porosimetry using a Pore Master GT33 from QUANTACHROME.

Example 1

10 mL of alumina catalyst (catalyst A, Na content=0.25% by weight in terms of $Na_2O$, Si content=0.06% by weight in terms of $SiO_2$, specific surface area=402 m$^2$/g, total pore volume=0.21 cc/g, pore volume of pores having a pore radius of at least 70 Å=78% of the total pore volume) that had been formed into spheres with diameters of from 2 to 5 mm was packed into a vertical tubular reactor tube, which is formed of SUS316, and which has an inner diameter=10 mm, and a length=30 cm, that had an electric oven on the outside and the electric oven temperature was set at 360° C. An 85% by weight of aqueous TBA solution, which was produced by the selective hydration of the isobutene out of a hydrocarbon mixture containing isobutene and n-butene, using an aqueous catalyst solution containing water and heteropolyacid catalyst, was preheated to 100° C. and was fed from a top of the reactor at 20 mL/hr (LHSV=2.0 hr$^{-1}$) and a reaction was run while maintaining a pressure within the reaction tube at 4 kg/cm$^2$·G. The gas/liquid mixture discharged from a bottom of the reaction tube was separated into a liquid phase portion and a gas phase portion. After the elapse of prescribed periods of time after the start of the experiment, the reaction product in the gas phase portion was analyzed by a gas chromatography to determine the reaction performance. After 5 hours, the TBA conversion was 95%, the isobutene selectivity was 99%, and the yield was 94%. After 800 hours, the TBA conversion was 94%, the isobutene selectivity was 99%, and the yield was 93%.

Example 2 and Comparative Examples 1 to 5

Performance evaluations were carried out under entirely the same reaction conditions as in Example 1 using various alumina catalysts (catalysts B, C, D, E, F, and G) with different properties as the catalyst. The results are shown in Table 1. Main by-products were disobutene and sec-butanol.

It is shown in Table 1 that catalysts A and B gave the highest isobutene yields and in particular the highest isobutene yields after 800 hours.

Example 3

10 mL of catalyst A was packed in the reaction tube used in Example 1 and the temperature of the electric oven was set to 250° C. The 85% by weight of aqueous TBA solution used in Example 1 was preheated to 100° C. and was fed from the top of the reactor at 5 mL/hr (LHSV=0.5 hr$^{-1}$) and a reaction was run while maintaining the pressure within the reaction tube at 4 kg/cm$^2$·G. The results are shown in Table 2.

Example 4

10 mL of catalyst A was packed in the reaction tube used in Example 1 and the temperature of the electric oven was set to 400° C. The 85% by weight of aqueous TBA solution used in Example 1 was preheated to 100° C. and was fed from the top of the reactor at 10 mL/hr (LHSV=1.0 hr$^{-1}$) and a reaction was run while maintaining the pressure within the reaction tube at 4 kg/cm$^2$·G. The results are shown in Table 2.

Comparative Examples 6 and 7

Reactions were run by setting the temperature of the electric oven in Example 2 to 150° C. and the temperature of the electric oven in Example 3 to 500° C., while keeping the other reaction conditions entirely the same. The results are shown in Table 2.

Example 5

600 mL catalyst A was packed into a vertical tubular reactor tube, which is formed of SUS316, and which has an inner diameter=25.4 mm, and a length=280 cm, that had an oil heating tank on the outside and the electric oven temperature was set at 350° C. The 85% by weight of aqueous TBA solution used in Example 1 was preheated to 100° C. and was fed from the top of the reactor at 600 mL/hr (LHSV=1.5 hr$^{-1}$) and a reaction was run while maintaining the pressure within the reaction tube at 4 kg/cm$^2$·G. A catalyst life test was run under these conditions, and the results of the reaction at total reaction times of 1800 hours and 9000 hours are shown in Table 3.

Comparative Examples 8 to 10

Performance evaluations were carried out using entirely the same catalyst and entirely the same reaction conditions as in Example 1, with the exception that the aqueous TBA solution as the starting material was changed. Comparative Example 8 used TBA produced as a by-product during the production of propylene oxide, Comparative Example 9 used TBA obtained by hydration in the presence of acetic acid over an ion-exchange resin from the hydrocarbon mixture that contained isobutene and n-butene; and Comparative Example 10 used TBA obtained by hydration over an ion-exchange resin from the hydrocarbon mixture that contained isobutene and n-butene. The results at a total reaction time of 800 hours are shown in Table 4, which for purposes of comparison also shows the composition of the TBA and the reaction results from Example 1.

TABLE 1

|  | EXAMPLE 1 | | EXAMPLE 2 | | COMP. EXAMPLE 1 | | COMP. EXAMPLE 2 | | COMP. EXAMPLE 3 | | COMP. EXAMPLE 4 | | COMP. EXAMPLE 5 | |
| --- | --- | --- | --- | --- | --- | --- | --- | --- | --- | --- | --- | --- | --- | --- |
| LHSV (hr$^{-1}$) | 2 | | 2 | | 2 | | 2 | | 2 | | 2 | | 2 | |
| TEMPERATURE (° C.) | 360 | | 360 | | 360 | | 360 | | 360 | | 360 | | 360 | |
| PRESSURE (kg/cm$^2$·G) | 4 | | 4 | | 4 | | 4 | | 4 | | 4 | | 4 | |
| CATALYST | A | | B | | C | | D | | E | | F | | G | |
| SPECIFIC SURFACE AREA (m$^2$/g) | 402 | | 391 | | 368 | | 389 | | 178 | | 327 | | 376 | |
| TOTAL PORE VOLUME (cc/g) | 0.21 | | 0.19 | | 0.30 | | 0.32 | | 0.41 | | 0.08 | | 0.27 | |
| PROPORTION IN THE TOTAL PORE VOLUME OF PORES HAVING A PORE RADIUS OF AT LEAST 70 A (%) | 78 | | 74 | | 73 | | 74 | | 84 | | 53 | | 75 | |
| Na$_2$O (wt %) | 0.25 | | 0.13 | | 0.68 | | 0.33 | | 0.31 | | 0.65 | | 0.05 | |
| SiO$_2$ (wt %) | 0.06 | | 0.35 | | 0.13 | | 0.52 | | 0.08 | | 0.09 | | 0.36 | |
| REACTION TIME (hr) | 5 | 800 | 5 | 800 | 5 | 800 | 5 | 800 | 5 | 800 | 5 | 800 | 50 | 800 |
| CONVERSION (%) | 95 | 94 | 97 | 95 | 81 | 75 | 98 | 78 | 82 | 74 | 78 | 66 | 98 | 79 |
| SELECTIVITY (%) | 99 | 99 | 97 | 95 | 97 | 95 | 91 | 88 | 99 | 97 | 97 | 94 | 89 | 85 |
| YIELD (%) | 94 | 93 | 94 | 90 | 79 | 71 | 89 | 69 | 81 | 72 | 76 | 62 | 87 | 67 |

TABLE 2

|  | EXAMPLE 3 | | EXAMPLE 4 | | COMP. EXAMPLE 6 | | COMP. EXAMPLE 7 | |
| --- | --- | --- | --- | --- | --- | --- | --- | --- |
| LHSV (hr$^{-1}$) | 0.5 | | 1 | | 0.5 | | 1 | |
| TEMPERATURE (° C.) | 250 | | 400 | | 150 | | 500 | |
| PRESSURE (kg/cm$^2$ · G) | 4 | | 4 | | 4 | | 4 | |
| CATALYST | A | | A | | A | | A | |
| REACTION TIME (hr) | 5 | 300 | 5 | 300 | 5 | 300 | 5 | 300 |
| CONVERSION (%) | 86 | 86 | 100 | 100 | 57 | 58 | 100 | 85 |
| SELECTIVITY (%) | 98 | 98 | 99 | 99 | 79 | 78 | 77 | 75 |
| YIELD (%) | 84 | 84 | 99 | 99 | 45 | 45 | 77 | 64 |

TABLE 3

|  | EXAMPLE 5 | | |
| --- | --- | --- | --- |
| LHSV (hr$^{-1}$) | 1 | | |
| TEMPERATURE (° C.) | 350 | | |
| PRESSURE (kg/cm$^2$ · G) | 4 | | |
| CATALYST | A | | |
| REACTION TIME (hr) | 5 | 1800 | 9000 |
| CONVERSION (%) | 100 | 100 | 98 |
| SELECTIVITY (%) | 99 | 99 | 99 |
| YIELD (%) | 99 | 99 | 97 |

TABLE 4

|  | EXAMPLE 1 | | COMP. EXAMPLE 8 | | COMP. EXAMPLE 9 | | COMP. EXAMPLE 10 | |
| --- | --- | --- | --- | --- | --- | --- | --- | --- |
| TBA PURITY (wt %) | 85.0 | | 97.4 | | 85.9 | | 86.7 | |
| WATER CONCENTRATION (wt %) | 14.9 | | 0.7 | | 13.2 | | 13.2 | |
| DIISOBUTENE CONCENTRATION (wt %) | 0.01 | | 0.02 | | 0.01 | | 0.03 | |
| KETONES CONCENTRATION (wt %) | 0 | | 1.7 | | 0 | | 0 | |
| BUTYL ACETATES CONCENTRATION (wt %) | 0 | | 0 | | 0.8 | | 0 | |
| REACTION TIME (hr) | 5 | 800 | 5 | 800 | 5 | 800 | 5 | 800 |
| CONVERSION (%) | 95 | 94 | 93 | 83 | 95 | 89 | 95 | 91 |
| SELECTIVITY (%) | 99 | 99 | 99 | 93 | 99 | 96 | 99 | 98 |
| YIELD (%) | 94 | 93 | 92 | 77 | 94 | 85 | 94 | 89 |

Reference experiments used in the examples of TBA production according to the present invention are as follows.

Reference Experiment 1

Analysis of the Accumulating Impurity

Figure 1:
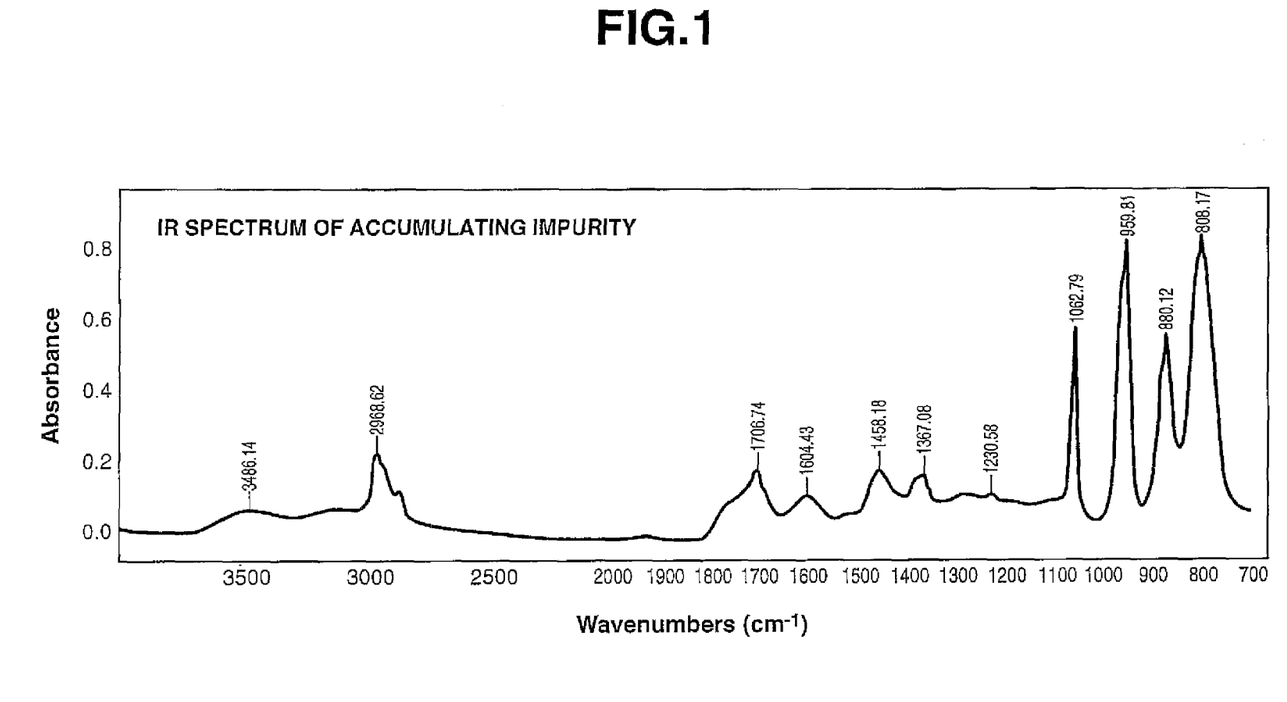
FIG. 1 shows the infrared absorption spectrum of accumulating impurity yielded by the TBA production process.

Causative Substance for Surface-Active Behavior 1000 g of an aqueous catalyst solution that contained approximately 50% by weight of phosphomolybdic acid and that had been used in the continuous reaction for approximately 1 year, was brought into contact with 250 g of the bead-form adsorbent (Sepabeads SP207 from Mitsubishi Chemical, modified styrene type, specific surface area=630 m$^2$/g, highest frequency pore diameter=21 nm) for 3 hours at approximately 60° C. white mixing. The adsorbent was then separated by filtration and was washed with distilled water until the wash water became colorless and transparent. The adsorbent was then dried in an air current followed by immersion in a 1000 mL of acetone solution and standing for about 1 hour. The resulting acetone solution became a yellowish brown color. The acetone was removed from this yellowish brown acetone solution at 60° C. under a reduced pressure using a rotary evaporator, yielding a yellowish brown solid material. The results of elemental analysis on this yellowish brown solid material showed it to be a material composed of phosphorus, molybdenum, carbon, nitrogen, and hydrogen. The infrared absorption spectrum of this substance was measured to yield a spectrum. The infrared absorption spectrum of the accumulating impurity obtained by the present invention is shown in FIG. 1. This infrared absorption spectrum presents absorptions at 1062 cm$^{-1}$, 960 cm$^{-1}$, 880 cm$^{-1}$, and 808 cm$^{-1}$ that are characteristic of Keggin-type heteropolyacids and absorptions originating with organic compounds, inter alia, the C—H stretching vibration at 2970 cm$^{-1}$, and a compound containing both alkyl and an anion could thus be confirmed as an accumulating impurity.

Reference Experiment 2

Evaluation of Separation Behavior 50 mL of a 50% by weight of aqueous phosphomolybdic acid solution prepared from fresh reagents and 50 mL of a raffinate containing 43% by weight of isobutene were introduced into a pressure-resistant glass container and were mixed by vigorous shaking for 3 minutes; shaking was then stooped and the time required for an interface to form was measured. As a result of 5 runs, an average of 6 seconds was required for separation into 2 phases and formation of an interface.

Reference Experiment 3

Evaluation of Separation Behavior 0.5 g of the accumulating impurity obtained in Reference Experiment 1 was added to 50 mL of 50% by weight of aqueous phosphomolybdic acid solution prepared from the fresh reagents, and this and 50 mL of a raffinate containing 43% by weight of isobutene were introduced into a pressure-resistant glass container and were mixed by vigorous shaking for 3 minutes; shaking was then stopped and the time required for an interface to form was measured. As a result of 5 runs, an average of 120 seconds was required for separation into 2 phases and formation of an interface; in addition, the interface was indistinct.

Example 6

Figure 2:
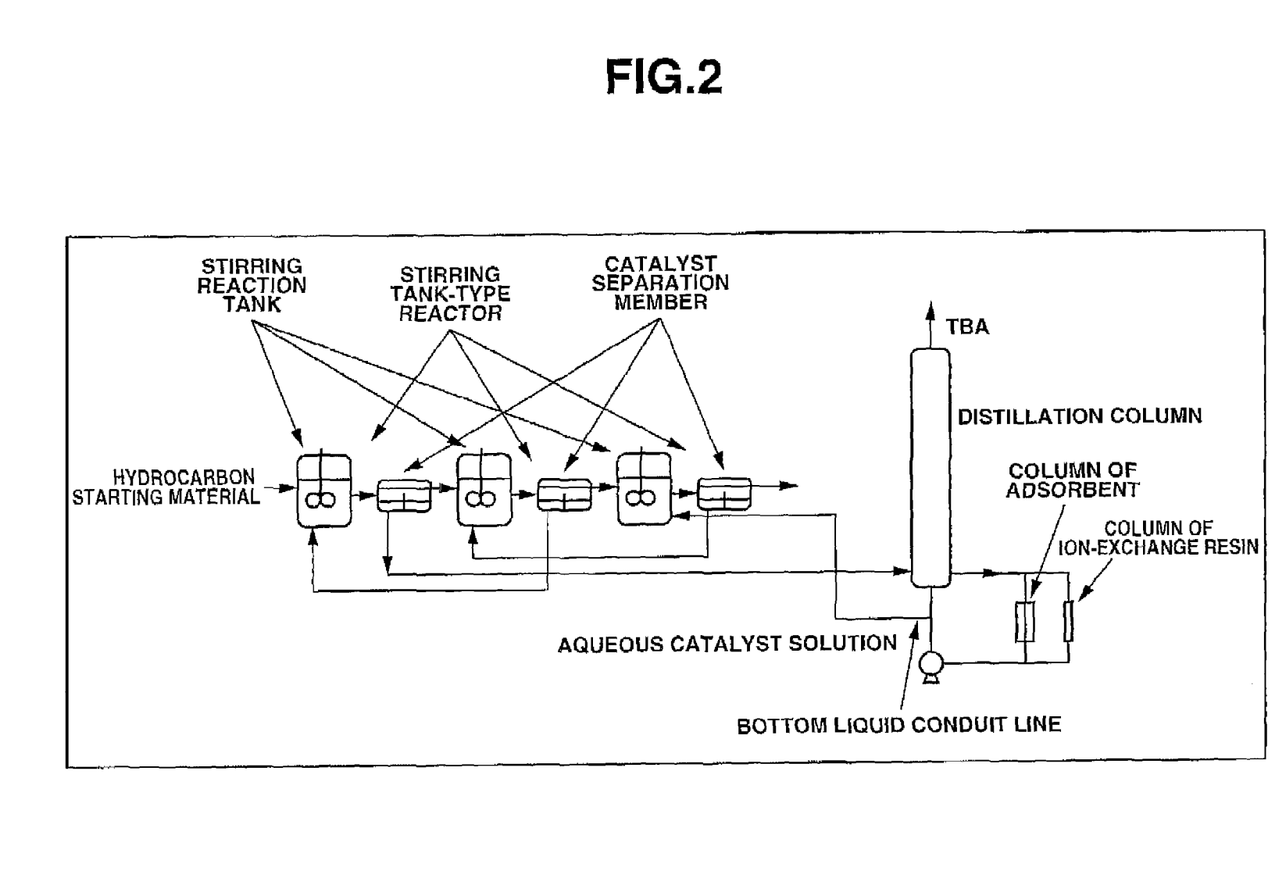
FIG. 2 shows the continuous production apparatus that is one aspect for carrying out the TBA production process according to the present invention.

FIG. 2 shows an example of the continuous production apparatus as one aspect for carrying out the TBA production process according to the present invention. In this continuous production apparatus for the present invention, elements such as the stirring tank-type reactors, pipes, and the like are all made of SUS304 (18.0% Cr, 8.0% Ni, no more than 0.08% C), and there are provided three stirring tank-type reactors, each of which is constituted of a stirring reaction tank with a 10 L reaction volume and a catalyst separation member with a volume of 2 L. While the example in FIG. 2 has three stirring tank-type reactors, the continuous production apparatus according to the present invention is provided with at least one stirring tank-type reactor and is not limited to an apparatus provided with three stirring-type reactors. A process was run in which the particular hydrocarbon phase (oil phase) and aqueous catalyst solution (aqueous phase) were separated at the catalyst separator disposed at each reactor; the hydrocarbon as the starting material and aqueous catalyst solution were reacted in a counterflow manner; the TBA product-containing aqueous catalyst solution separated at the catalyst separator of the final reaction tank was fed to a packed column-type distillation column having 20 theoretical plates; TBA was separated from a top of the distillation column; control was carried out to give a reduced pressure such that the bottom temperature was 70° C.; and aqueous catalyst solution was recovered from the bottom. In addition, the following were disposed in the bottom liquid conduit line: a column packed with 500 mL of acid-form cation-exchange resin (SK1B from Mitsubishi Chemical) and adsorbent in a form of a synthetic resin system (Sepabeads P207 from Mitsubishi Chemical, highest frequency pore diameter=21 nm, fill quantity=500 mL). An amount of liquid that was about one-tenth the amount of bottom liquid was circulated, and the aqueous catalyst solution was supplied to the stirring tank-type reactors while continuously carrying out adsorptive removal of the impurity metal ion and the accumulating impurity (refer to FIG. 2). As the catalyst, a 50% by weight of fresh phosphomolybdic acid ($H_3PMo_{12}O_{40}$) solution (Hammett acidity function $H_0$: $-5.6 \geq H_0$) was prepared and fed at 50 L/h to all of the reactors shown as illustrated in FIG. 2; as the hydrocarbon starting material, a raffinate 1 containing 43% by weight of isobutene was fed in a counterflow manner at 20 L/h. With regard to the reaction temperature, control was carried out such that the stirring reaction tank in each reactor was at 70° C. At each 48-hour interval after the start of the reaction, an intermittent procedure was carried out in which 100 mL of 10% by weight of aqueous hydrogen peroxide was fed over 1 hour into the distillation column bottom conduit. Continuous operation was carried out for approximately 2000 hours. The isobutene conversion was 95% and the selectivity for TBA (water removed) was 99% in the initial phase of the reaction, and almost the same reaction results were maintained even after 2000 hours had elapsed. In addition, the following were completely absent: outflow of the catalyst into unreacted hydrocarbon due to a deterioration in the catalyst separation performance at the catalyst separator, and a deterioration in operability accompanying a rise in the pressure difference in the distillation column. 50 mL of the aqueous catalyst solution at this point was brought into contact with 30 mL of fresh Sepabeads adsorbent in order to adsorb the quantity of accumulating impurity. Then, using the same procedure as in Reference Example 1, the adsorbent was washed with water and separated, the accumulating impurity was dissolved from the adsorbent using acetone, and the acetone was evaporated to give a residue taken to be the amount of impurity. According to this procedure, the amount of accumulating impurity in the aqueous catalyst solution was 2.1% by weight.

Comparative Example 11

A continuous reaction was carried out by the same process as in Example 6, but in this case without disposing the column of acid-form cation-exchange resin and the column of adsorbent in the bottom liquid conduit line as was done in Example 6. A conversion of 95% was maintained at 100 hours after the start of the reaction; however, beginning at about 150 hours, a rise in the pressure difference in the distillation column was observed and some turbidity was also observed in the unreacted hydrocarbon. Molybdenum was detected when the unreacted hydrocarbon was evaporated and the residue was analyzed by X-ray fluorescence. The reaction was stopped because the decline in separation performance at the catalyst separation members and the deterioration in separation at the distillation column made it quite difficult to continue the reaction. After the reaction had been stopped, aqueous catalyst solution was withdrawn and the catalyst separation performance was tested as in Reference Experiment 2. According to the results for 5 runs, an average of 160 seconds was required until separation into 2 phases and formation of the interface; moreover, the interface was also indistinct, 50 mL of this aqueous catalyst solution was brought into contact with 30 mL of fresh Sepabeads adsorbent in order to adsorb the quantity of accumulating impurity. When the quantity of accumulating impurity was then determined by the same procedure as in the reference examples, the quantity of accumulating impurity in the aqueous catalyst solution was 11.5% by weight.

Example 7

A reaction was run using the same procedure as in Example 6, but in this case without carrying out the oxidation treatment using hydrogen peroxide. The isobutene conversion was 95% at about the tenth hour from the beginning of the reaction. A stable reaction operation could be maintained and long-term operation was possible. However, a gentle decline in activity was seen from about 500 hours; the isobutene conversion at about hour 1000 was 94.2% and after the elapse of 2000 hours was 93.6% and a decline in activity was seen in the long-term reaction.

Example 8

The same procedure as in Example 6 was carried out, but in this case changing the material of the stirring vessels to Hastelloy B (67% Ni, 28% Mo, 5% Fe), which generally has a better resistance to acid corrosion than SUS304. The ion-exchange resin was also not installed in this case. The isobutene conversion was 95% at about the tenth hour from the beginning of the reaction. A stable reaction operation could be maintained and long-term operation was possible. However, a gentle decline in activity was seen from about 300 hours; the isobutene conversion at about hour 1000 was 94.5% and after the elapse of 2000 hours was 94.1% and a decline in activity was seen in the long-term reaction. When the aqueous catalyst solution was analyzed after the reaction had been stopped, the iron ion had increased about 700 ppm to 800 ppm and the result predicted from the general corrosion resistance was confirmed.

Example 9

Figure 3:
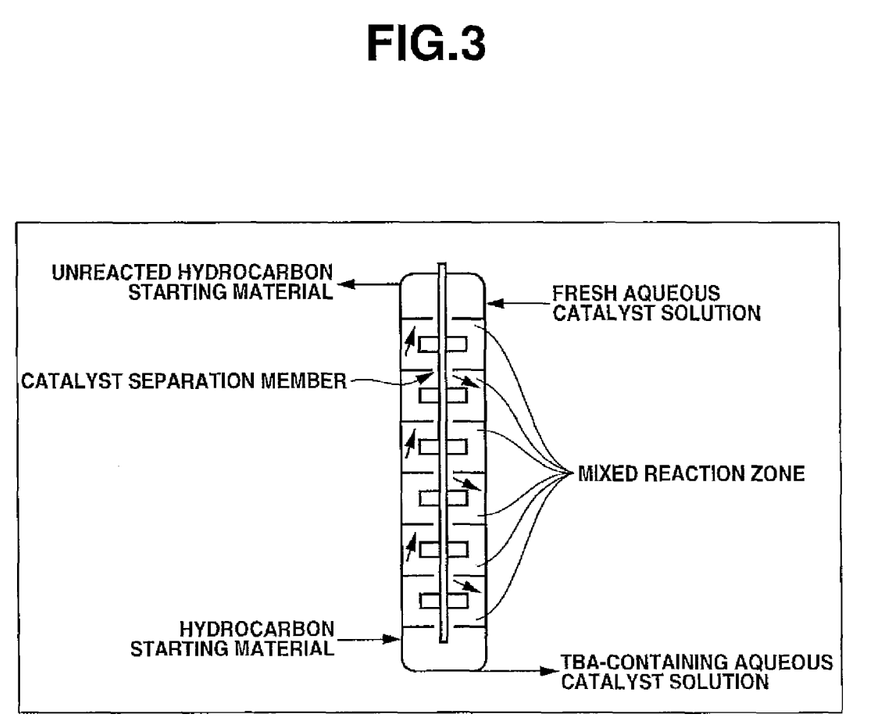
FIG. 3 shows the schematic diagram of an example of a reactor used in the TBA production process according to the present invention.

The reaction was carried out in the same manner, but changing the 3 reactors in Example 6 to 1 counterflow-type reactor with the structure shown in FIG. 3 that had 8 mixing reaction zones (volume of each mixing reaction zone=15 L). Given the fact that a high isobutene conversion value of 97.5% was obtained, a high reactivity could be confirmed for the method of feeding the catalyst and the starting material in a counterflow manner and for the counterflow-type reactor.

Example 10

A 500-hour reaction was run using the same procedure as in Example 6, but in this case changing the catalyst to phosphotungstic acid ($H_3PW_{12}O_{40}$) and establishing the same proton concentration. The isobutene conversion was 95.2% after a 10-hour reaction and was 95.2% even after the elapse of 500 hours, and operability problems were also entirely absent.

Example 11

A 500-hour reaction was run using the same procedure as in Example 6, but in this case changing the catalyst to phosphovanadomolybdic acid ($H_4PVMo_{11}O_{40}$) and establishing the same proton concentration. The isobutene conversion was 94.7% after a 10-hour reaction and was 94.8% even after the elapse of 500 hours, and operability problems were also entirely absent.

Example 12

A 500-hour reaction was run using the same procedure as in Example 6, but in this case changing the catalyst to silicotungstic acid ($H_4SiW_{12}O_{40}$) and establishing the same proton concentration. The isobutene conversion was 95.3% after a 10-hour reaction and was 95.2% even after the elapse of 500 hours, and operability problems were also entirely absent.

Example 13

The same procedure as in Example 6 was carried out, but in this case changing the material of the stirring vessels from SUS304 to SUS316 (18.0% Cr, 10.0% Ni, no more than 0.08% C, 2.0% Mo), which additionally contained a small amount of molybdenum. The ion-exchange resin was also not installed in this case. The isobutene conversion was 95.2% at about the tenth hour from the beginning of the reaction. A stable reaction operation could be maintained and long-term operation was possible. The decline from about 300 hours was also not seen, and the isobutene conversion at about hour 1000 was 95.1% and after the elapse of 2000 hours was 95.2% and an activity decline was thus not seen even in the long-term reaction. When the aqueous catalyst solution was analyzed after the reaction had been stopped, the iron ion, at 98 ppm, was not observed to have undergone a significant increase from the beginning.

INDUSTRIAL APPLICABILITY

The isobutene production process according to the present invention provides a high-yield, high-selectivity, and long-term stable process for producing isobutene from TBA. Further, the TBA production process according to the present invention provides a TBA production process in which, through long-term stable maintenance of a high reaction activity, long-term continuous operation is made possible and the productivity is improved. Furthermore, the present invention can substantially reduce catalyst losses and the production losses associated with stopping operations and achieves energy savings and waste reduction.

We claim:

1. A process for continuously producing tert-butanol, the process comprising:
   (a) producing tert-butanol from a hydrocarbon mixture containing isobutene and n-butene by selectively hydrating the isobutene using an aqueous catalyst solution comprising water and a catalyst, the producing being performed in a reactor;
   (b) providing a distillation column with the hydrocarbon mixture, the catalyst, and the tert-butanol and distilling thereof;
   (c) removing a portion of accumulating impurity with a porous adsorbent used with the ion-exchange resin from a first bottom liquid remained in the distillation column; and
   (d) supplying the reactor with a second bottom liquid obtained from the first bottom liquid by the (c) removing the accumulating impurity.

2. The production process according to claim 1, wherein a pore radius of the porous adsorbent is in a range of 0.5 to 500 nm.

3. The production process according to claim 1, wherein the catalyst is a strong acid or a strong acid salt that exhibits $-5.6 \geq H_0$ where $H_0$ is the Hammett acidity function.

4. The production process according to claim 1, wherein the catalyst is a heteropolyacid which is selected from the group consisting of phosphomolybdic acid, phosphomolybdovanadic acid, phosphotungstic acid, phosphotungstovanadic acid, silicotungstic acid, salt thereof, and a mixture thereof.

5. The production process according to claim 4, wherein the ion-exchange resin is a cation-exchange resin.

6. The production process according to claim 1, further comprising: reacting the aqueous catalyst solution and the hydrocarbon mixture while feeding the aqueous catalyst solution and the hydrocarbon mixture into a reactor in a counterflow manner.

7. The production process according claim 1, further comprising: continuously or discontinuously adding an oxidizing agent.

* * * * *

UNITED STATES PATENT AND TRADEMARK OFFICE
CERTIFICATE OF CORRECTION

PATENT NO. : 8,637,716 B2  
APPLICATION NO. : 12/091016  
DATED : January 28, 2014  
INVENTOR(S) : Tatsuo Yamaguchi et al.

Page 1 of 1

It is certified that error appears in the above-identified patent and that said Letters Patent is hereby corrected as shown below:

ON THE TITLE PAGE:

At item (75), Inventors, change "Shumya Kirino, Chiyoda-ku (JP)" to --Shunya Kirino, Chiyoda-ku (JP)--.

Signed and Sealed this
Eighth Day of July, 2014

Michelle K. Lee
*Deputy Director of the United States Patent and Trademark Office*